United States Patent [19]

Pelosi, Jr.

[11] 4,097,500

[45] Jun. 27, 1978

[54] N-METHYL-5-(4-NITROPHENYL)-N-(A-METHYLPHENETHYL)FURFURYLAMINE HYDROCHLORIDE

[75] Inventor: Stanford S. Pelosi, Jr., Norwich, N.Y.

[73] Assignee: Morton-Norwich Products, Inc., Norwich, N.Y.

[21] Appl. No.: 818,527

[22] Filed: Jul. 25, 1977

[51] Int. Cl.² .................................... C07D 307/52
[52] U.S. Cl. .............................. 260/347.7; 424/285
[58] Field of Search ................................. 260/347.7

[56] References Cited

FOREIGN PATENT DOCUMENTS 1,241,399   8/1960   France ........................... 260/347.7

OTHER PUBLICATIONS

Novilskii et al., Zhur Obshch. Khim. 32(6), 1962, 1824–1828.

Primary Examiner—Richard L. Raymond
Attorney, Agent, or Firm—Anthony J. Franze

[57] ABSTRACT

N-Methyl-5-(4-nitrophenyl)-N-(a-methylphenethyl)furfurylamine hydrochloride is useful as an antidepressant agent.

1 Claim, No Drawings

N-METHYL-5-(4-NITROPHENYL)-N-(A-METHYL-PHENETHYL)FURFURYLAMINE HYDROCHLORIDE

This invention relates to the compound N-methyl-5-(4-nitrophenyl)-N-(a-methylphenethyl)furfurylamine hydrochloride.

The compound of this invention is useful as an antidepressant agent. Its useful antidepressant activity is exhibited in warm blooded animals under the standard ptosis-anti-tetrabenazine test. Thus, when administered perorally in suspension or aqueous solution in a dose of 50 mg/kg to mice shortly prior to intraperitoneal administration of from 1–10 mg/kg of tetrabenazine, ptosis induced by tetrabenazine is curtailed to the extent of 100%.

This compound is preferably prepared in accordance with the following example:

A solution of 11.9 g (0.05 mole) of 5-(4-nitrophenyl)-furfuryl chloride and 14.9 g (0.10 mole) of d-N,a-dimethylphenethylamine in 60 ml of benzene was heated under reflux for 7 hrs. After standing overnight, the solid N,a-dimethylphenethylamine hydrochloride (9 g, 97%) was collected by filtration and washed with benzene. The benzene filtrate was washed with 10% $Na_2CO_3$ and water and dried over $MgSO_4$. The solvent was removed on a rotary evaporator, and the residual oil was dissolved in 100 ml of anhydrous ether and 35 ml of nhydrous MeOH. The solution was treated with 20 ml of ethereal HCl and diluted with ether to give an oil. The solvent was removed on a rotary evaporator, and the residual oil was dissolved in ethyl acetate with heating. Cooling gave an oil which was dissolved by the addition of MeOH and 10 ml of etheral HCl. After cooling and dilution with ether, the yellow solid which was deposited was collected by filtration to give 13 g (67%) of N-methyl-5-(4-nitrophenyl)-N-(a-methylphenethyl)furfurylamine hydrochloride; m.p. 168°–175°.

Anal. Calcd. for $C_{21}H_{22}N_2O_3 \cdot HCl$: C, 65.19; H, 5.99; N, 7.24. Found: C, 65.17; H, 6.09; N, 7.29.

What is claimed is:

1. The compound N-methyl-5-(4-nitrophenyl)-N-(a-methylphenethyl)-furfurylamine hydrochloride.

* * * * *